United States Patent [19]

Taylor et al.

[11] Patent Number: 4,975,364
[45] Date of Patent: Dec. 4, 1990

[54] DETERMINING SEED VIABILITY

[75] Inventors: Alan G. Taylor, Geneva, N.Y.; Henry J. Hill, Fresno, Calif.; Xue-lin Huang, Guangzhou, Rep. of China; Tai-gi Min, Geneva, N.Y.

[73] Assignee: Cornell Research Foundation, Inc., Ithaca, N.Y.

[21] Appl. No.: 259,688

[22] Filed: Oct. 19, 1988

[51] Int. Cl.$^5$ .................. C12Q 1/00; C12Q 1/02; A01C 1/02
[52] U.S. Cl. ......................................... 435/4; 435/29; 436/172; 47/57.6
[58] Field of Search ............... 435/4, 34, 29; 436/172; 47/57.6, DIG. 11

[56] References Cited

PUBLICATIONS

Sincar et al., "Role of Endogenous Ferrule & Sinapic Acids . . . ", Chem. Abst. 76(1), #18725, pp. 180–181, Jan. 3, 1972.
Handout From the "Seed Research Open House", Apr. 1, 1987, NYS Agri. Experiment Station, Geneva, NY.
Austin et al., 1968, J. Agr. Food Chem., 16:132–135.
Blair et al., 1984, J. Sci, Food Agric., 35:29–35.
Takayanagi et al., 1969, Proc. Internat. Seed Testing Association, 34:243–252.
Schoettle et al., 1984, Crop Sci., 24:835–838.
Dabrowski et al., 1984, J. Agric. Food Chem., 32:123–127.
Durkee et al., 1975, J. Food Sci., 40:820–822.
Powell et al., 1977, J. Exp. Bot., 28:225–234.
Samad et al., 1978, J. Exp. Botany, 29:1471–1478.
Spaeth, 1987, Plant Physiol., 85:217–223.
Dadlani et al., 1983, Scientia Hort., 19:39–44.
Simon et al., 1972, J. Exp. Botany, 23:1076–1085.
Leopold, 1980, Plant Physiol., 65:1096–1098.
Powell et al., 1981, J. Exp. Botany, 32:1045–1050.
McKersie et al., 1980, Plant Physiol., 66:316–320.
Murphy et al., 1982, Plant Physiol., 69:428–431.
Powell et al., 1979, J. Exp. Botany, 30:193–197.
Duke et al., 1981, Plant Physiol., 67:449–456.
Harman et al., 1972, Physiol. Plant Path., 2:271–278.
Duke et al., 1983, Plant Physio., 72:919–924.
Hepburn et al., 1984, Seed Sci. and Tech., 12:403–413.
Tzagoloff, 1963, Plant Physiol., 38:202–206.
Kugler, 1952, Naturwissenschaften, 39:213.
Zheng et al., 1964, Bol. Plant Physio., 3:21–25.
Lesage, 1911, Comp. Rendus, 152:615–617.
Lesage, 1922, Comp. Rendus, 174:766–767.

*Primary Examiner*—Esther L. Kepplinger
*Assistant Examiner*—Carol Bidwell
*Attorney, Agent, or Firm*—Jones, Tullar & Cooper

[57] ABSTRACT

A method of determining the viability of crucifer seed, for example cabbage seed by detecting leakage of sinapine from non-viable seeds.

5 Claims, 4 Drawing Sheets

DETERMINING SEED VIABILITY

BACKGROUND OF THE INVENTION

Seeds leak a wide range of compounds when imbibed in water including carbohydrates, proteins and inorganic ions (Samad and Pearce, 1978, *J. Exper. Botony*, 29:1471–1478) and larger intracellular substances such as starch, grains and protein bodies (Spaeth, 1987, *Plant Physio.*, 85:217–223). Differential leakage of specific compounds has been associated with seed viability in some species. The percentage of water soluble carbohydrates was negatively correlated with germination in carrot (*Daucus carota* L.) (Dadlani and Agrawal, 1983, *Scientia Hort.*, 19:39–44). Fructose, glucose, sucrose, maltose, raffinose and stachyose were identified in the leachate from non-viable rape (*Brassica napus* L.) seeds (Takayanagi and Murakami, 1969, *Proc. Internat. Seed Testing Assoc.*, 34:243–252). Viable seeds leaked only trace amounts of fructose and glucose. Artificially aged soybean (*Glycine max* L. Merr) seeds were observed to leak higher amounts of compounds that absorbed light at 260 nm than non-aged seeds (Schoettle and Leopold, 1984, *Crop Sci.*, 24:835–838).

Phenolic compounds have been found in seeds. Sinapine, the choline ester of sinapic acid (3,5-dimethoxy-4-hydroxycinnamic acid) (Austin and Wolff, 1968, *J. Agr. Food. Chem.*, 16:132–135), has been found among various species of Brassicaceae (Cruciferae) (Schultz and Gmelin, 1952, *Z. Naturforschung*, 7b:500–508), and is the main phenolic constituent of rape seed occurring at levels from 1.0–2.5 percent dry matter (Blair and Reichert, 1984, *J. Sci. Food. Agri.*, 35:29–35). The compound is fluorescent under UV light and becomes yellow at high pH ($>10$). Hydrolysis products of sinapine are sinapic acid and choline which are metabolized during germination (Tzagoloff, 1963, *Plant Physio.*, 38:202–206).

Non-viable or deteriorated seeds have been reported to leak more solutes when placed in water than viable or vigorous seeds (Simon and Harun, 1972, *J. Ex. Botany*, 23:1076–1085; Leopold, 1980, *Plant Physio.*, 65:1096–1098; Powell and Matthews, 1981, *J. Ex. Botany*, 32:1045–1050). Aged, damaged, or non-functional cellular membranes (Simon and Harun, 1972, *supra*; McKersie and Stinson, 1980, *Plant Physio.*, 66:316–320; Murphy and Noland, 1982, *Plant Physio.*, 69:428–431) and cellular rupture caused by imbibition damage (Powell and Matthews, 1979, *J. Ex. Botany*, 30:193–197; Duke and Kakefuda, 1981, *Plant Physio.*, 67:449–456) have been suggested as major causes.

Among the solutes leaked from seeds of various species are; free amino acids (Harman and Granett, 1972, *Physiol. Plant Path.*, 2:271–278), proteins (McKersie and Stinson, 1980, *supra*), sugars (Takayanagi and Murakami, 1969, *supra*), and phenolics (Samad and Pearce, 1978, *supra*). Ions and inorganic compounds of potassium, phosphate, and magnesium are also leaked (Simon and Harun, 1972, *supra*; Samad and Pearce, 1978, *supra*; McKersie and Stinson, 1980, *supra*). The two most common methods of measuring seed leakage are electrical conductivity and light absorption at specific wavelengths (Harman and Granett, 1972, *supra*; Duke, Kakefuda, and Harvey, 1983, *Plant Physio.*, 72:919–924; Hepburn, Powell, and Matthews, 1984, *Seed Sci. & Tech.* 12:403–413).

DESCRIPTION OF THE INVENTION

This invention relates to a method of determining the viability of crucifer seeds, for example cabbage seeds, by detecting leakage of sinapine, which leaks from non-viable seeds but is only excluded in small amounts, if at all, from viable seeds.

Crucifer (cruciferea) seeds, include agronomically significant crop seeds such as cabbage, cauliflower, broccoli, canola and others.

The method of the invention can be practiced in a number of ways. Examples including detecting leaked sinapine by UV irradiating, and detecting relative amounts of sinapine in an aqueous soak medium by color change of the medium. The method broadly is not critical so long as it relates sinapine leakage to non-viable seeds as compared to viable seeds.

In a preferred embodiment, crucifer seeds are coated with an inert or beneficial seed coat which absorbs sinapine, thereby retaining the sinapine and allowing for easy detection of non-viable seed and its separation from viable seed.

In an especially preferred embodiment of the invention crucifer seeds are first soaked in aqueous media for a time sufficient (usually at least several hours) to foster leakage of sinapine from the non-viable seeds, if present. The soaked seeds are then coated with a sinapine absorbing coating and then dried. Non-viable seeds are then detected by irradiating with UV light to cause fluorescence of sinapine. The presence and relative amount of non-viable seeds present in a mass of seeds can be determined and, if desired, the significantly fluorescent and thus non-viable seeds can be separated from the mass by suitable means, for example a directing means which moves seeds, dropping past a sensing means, in a selected direction based upon fluorescence/non-fluorescence.

As to the latter, some viable crucifer seeds leak low levels of sinapine, thus non-fluorescence in some cases is actually low-level fluorescence. However, the difference in amount of fluorescense (at least twice as much sinapine and usually very much more from non-viable seeds) makes separating between viable and non-viable seeds or quantifying relative amounts of both, a relatively easy task.

Where soaking or hydration is employed, that process can be the usual hydration step otherwise employed to enhance seed quality and add beneficial materials to the seed etc., in a manner known in the art. Otherwise, it can simply be a soak in an aqueous media for the purposes of this invention.

Where a coating technique is used, the coating technique can be a coating technique otherwise used in the seed industry, can be such a technique further adapted to accomplish this invention, or can be a coating specifically formulated to accomplish this invention.

The coating can be inert to the seed or beneficial to the seed. For the purposes of this invention, the coating or any component therein must not fluoresce at the same wavelengths as sinapine, so as to confuse or prevent detection of sinapine; and the coating must not react with sinapine so as to cause an inability to detect sinapine, if present.

A number of beneficial seed coats are known, as well as seed coating methods. Pesticides, fungicides etc., such as thiran can be applied in such a manner. The coating can be merely a polymer or non-volitile liquid or a particulate, powdery material which adheres to the seed, or can be a mixture of a binder or carrier with active ingredients. For the purpose of the invention the 'active ingredient' of the coating is a material which absorbs and/or retains sinapine so that it can be detected by fluorescence. This function can be performed by a binder or carrier itself or by an absorbent filler such as minerals, sand, clays, vermiculite, cellulose, etc. The absorbent binder can be cellulose based; methyl cellulose based etc.

EXAMPLE 1

This example documents and then identifies a fluorescent compound that leaks from non-viable cabbage (*Brassica oleracea* var. *capitata* L.) seeds.

MATERIALS AND METHODS

Cabbage seeds 'King Cole' were supplied by the Ferry-Morse Seed Co., Modesto, Calif., U.S.A. Heat-killed (HK) seeds were obtained by autoclaving a sample of seeds of the same seedlot at 121° C. for 20 minutes.

Viable and HK seeds were soaked for three hours in distilled water. Representative seeds were then submerged in a 1.5% (w/v) Laponite 508 gel (Laporte Inc., Saddle Brook, N.J., U.S.A.) for a period of 2 to 4 hours. Fluorescent leakage was photographed under UV light.

Seed leachates were obtained by soaking 5 g of viable (germination >96%) and HK seeds in 15 mL distilled and deionized (DD) water for 8 h. Aliquots of leachate solutions were filtered using Whatman No. 2 filter paper and then either diluted with DD water to a 1:30 ration (v/v) for studies at pH 7 or diluted with 200 mM sodium carbonate-bicarbonate buffer (1:30 ratio) for studies at pH 10. Absorbance of leachate solutions of pH 7 and 10 were measured with a Hewlett Packard 8452A diode array spectrophotometer.

Aqueous extracts of seed leachate were prepared from viable and HK seeds as previously described for the spectrophotometer. Isolation and characterization of fluorescent compounds from the leachate was conducted using paper chromatography. Sixty $\mu$L of leachate was applied on Whatman No. 3 chromatography paper and first developed with BAW (n-butanol: acetic acid: water, 4:1:5) followed by 6% acetic acid. The air dried chromatograms were examined with UV light (245 nm) and later exposed to ammonia vapor. The most prominent spot, spot three, was further studied. One mL of leachate from HK seeds was applied to chromatography paper. The paper was developed with BAW and the bright fluorescent band at Rf 5.6 was cut and eluted with 95% ethyl alcohol. The solvent was removed in a rotary evaporator at 45° C. under vacuum. The eluates were subjected to basic hydrolysis using 2N NaOH at room temperature for 4 hr (Durkee and Thivierge, 1975, *J. Food Sci.,* 40:820–822).

Sinapic acid standard was purchased commercially (Aldrich Chemical Co., Milwaukee, Wisc., U.S.A.). Sinapine is not commercially available, therefore reference samples were prepared for this study from rapeseed oilmeal (Agway Inc., Batavia, N.Y., U.S.A.). Sinapine was extracted from rapeseed oilmeal as sinapine thiocyanate and then converted to sinapine bisulfate. The melting point of our sample was 186°–188° C. as determined by a Fisher-Johns melting point apparatus which compares favorably with a mp. of 187°–188° C. reported in the literature.

The original spot 3, basic hydrolysis of spot 3, sinapic acid and sinapine were applied onto chromatography paper. Chromatograms were developed with the following solvents; either 6% acetic acid, BAW or $H_2O$. Rf values were recorded and chromatograms were later treated with $NH_3$ vapor. Dragendorff reagent and diazotized p-nitroaniline (DPN) were sprayed onto chromatograms to produce colored products.

RESULTS AND DISCUSSION

Documentation of Fluorescent Leakage from Cabbage Seeds

Preliminary germination studies with cabbage seeds revealed that during imbibition, non-germinable (i.e. dead seeds from seedlot) or HK seeds leaked a material that fluoresced when radiated with UV light. This fluorescent material was blue-green in color and appeared outside the seed after 3 h of imbibition. It has been reported that non-germinable seeds of *Sinapsis alba, Raphanus sativus, Lepidium sativium* and *Brassica pekinensis* leak fluorescent material while germinable ones do not (Kugler, 1952, *Naturwissenschaften*, 39:213; Zheng and Yan, 1964, *Bol. Plant Physio.*, 3:21–25).

Laponite is a synthetic magnesium silicate which produces a viscous solution when dispersed in water and was found to be well suited as a media gel to visualize the leakage. Heat killed and non-germinable seeds submerged in Laponite gel exhibited a fluorescent halo around the seed. Viable seeds did not leak this fluorescent material unless damage was done to cotyledons. The 1% solution suspended the seed during incubation and observation. Due to the colloidal nature of the Laponite, fluorescence was easily observed.

Identification and fluorescent compound

The absorption spectra of leakage (solution pH 7) from heat-killed (HK) cabbage seeds after 8 h of soaking, revealed increased absorbance in a band from 280 to 360 nm with a 322 nm peak that was not observed for viable seed leachate. Increasing the HK seed-leachate solution to pH 10 caused the solution to become yellow and caused the 322 nm absorption peak to shift to 388 nm. No comparable change in the absorption spectra or solution color was observed for the viable seed leachate solution.

No other gross spectra differences could be detected between the viable and HK seed leachate. Therefore, the fluorescent compound in the HK seed leachate may have been the compound responsible for the increased UV-light absorption in the 280 to 360 nm range (at pH 7).

Two dimensional paper chromatography was conducted on the HK seed leachate to isolate the fluorescent compound. Chromatography resolved one fluorescent spot from viable seed leakage and four fluorescent spots from the HK seed leakage. The fluorescent spots from HK seed leakage were all faint except for spot 3 which was bright green-blue. Spot 3 was studied further due to its observed intensity under UV-light.

Experiments were conducted to determine if spot 3 was sinapine. The absorption spectra of spot 3 was very similar to that of sinapine thiocyanate. At pH 7, both compounds had a first λmax of 324 nm and 326 nm, respectively. Both spot 3 and sinapine thiocyanate also underwent a similar bathochromic shift when solution pH was increased to pH 10, both solutions turned yellow. Further studies were performed to confirm the identity of spot 3. Using three different solvent systems, Rf values of spot 3 were found to be identical with those of sinapine thiocyanate. Color reactions of spot 3 under UV and visible light were also identical to sinapine thiocyanate both before and after exposure to ammonia vapor or after treatment with either DPN or Dragendorff reagent. After undergoing basic hydrolysis, spot 3 was found to have the same Rf value and color reactions as sinapic acid. The hydrolysis products of sinapine have been shown to be sinapic acid and choline (Austin and Wolff, 1968, supra).

Based on the above results from spectrophotometric and chromatographic experiments it was concluded that spot 3 was indeed sinapine. When compared to sinapine thiocyanate, spot 3 had similar absorption maxima and minima at pH 7 and 10 the same Rf values and color reactions. Alkaline hydrolysis of spot 3 produced Rf values and color reactions identical to sinapic acid. Fluorescent spots 1, 2 and 4 may be other types of phenolic compounds since small quantities of phenolics have been isolated in seeds of *Brassica napus* and *Brassica campestris* (Dabrowski and Sosulski, 1984, *J. Agric. Food Chem.*, 32:123–127). When isolated, sinapine had the same blue-green fluorescent color and the same absorption spectra (both at pH 7 and 10) as the HK seed leachate. Sinapine was therefore the major compound contributing to the fluorescence of the HK cabbage seed leachate.

One reflection, the leakage of sinapine from HK and non-germinable seeds is rational. Sinapine is the major phenolic compound in *Brassica* and *Sinapis* oilseeds (Durkee and Thivierge, 1975, *J. Food Sci.*, 40:820–822) and occurs in seeds of many species of Brassicaceae (Schultz and Gmelin, 1952, supra). The compound, found in the cotyledons but not the seed coat (Blair and Reichert, 1984, supra), is a reverse material that is hydrolyzed during the latter phases of germination (Tzagoloff, 1962, supra). However, little information is available concerning its cellular localization and distribution.

Sinapine is present in both viable and non-viable seeds. However, leakage is only observed from non-viable seeds. Leakage of compounds from seeds has been associated with severe membrane deterioration. Since cell membranes are assumed non-functional in HK seeds, sinapine would leak from cells due to lack of compartmentalization. The seed coat, though not containing sinapine, is apparently not a barrier and therefore sinapine leaks (by diffusion) into the environment.

Laboratory tests have been developed to determine the viability and vigor of a sample from a seedlot. Various color producing reagents have been used to assay the seed quality on a single seed basis. The tetrazolium test has been widely used for this purpose (Assoc. Off. Seed Anal., 1983). The reduction of 2,3,5-triphenyl tetrazolium chloride by dehydrogenase enzymes present in the seed tissues produces a red compound formazan. Formazan is water insoluble and the seed must be dissected to detect staining. The chemical reaction is also harmful to the seed and therefore tetrazolium cannot be used to upgrade seed quality.

Coating technologies have been employed with conventional seed conditioning equipment. Materials have been applied to seeds to remove contaminants from the desired crop seed. Iron powder and water have been sprayed onto smooth seeded crops such as clover. The powder adheres to rough seed coats or mucilaginous seed coats of other crop and weed seeds. A magnetic drum was used to separate the undesirable material from the desired crop seed. Differences in seed coat characteristics were exploited in this technique, not physiological differences associated with leakage.

EXAMPLE 2

The purpose of these studies were: first, to compare sinapine and electrolyte leakage from heat killed, non-viable and viable cabbage seeds; second, to determine if sinapine detection tests could more accurately distinguish viable from non-viable cabbage seeds than the conductivity method.

MATERIALS AND METHODS

Two untreated lots of hybrid cabbage seed 'King Cole' were supplied by Ferry-Morse Seed Co., Modesto, Calif., U.S.A. One seedlot was produced in 1984 (hereafter referred to as "old"), the other lot was produced in 1985 (hereafter referred to as "new"). Since seeds of both lots represented the $F_1$ offspring of the same parental cross, seeds of both seedlots were assumed to be near-genetically identical. Heat-killed (HK) seeds of both lots were produced by autoclaving seeds at 121° C. for 20 minutes.

Imbibition time course studies were performed on 4 replications of 100 HK and viable old lot seeds by submerging them in distilled, deionized (DD) water at 25° C. At hourly intervals, seeds were removed from the water, blotted dry, weighed, and returned to the water. Imbibition rates were expressed as percentage increase of the air-dry weight. Time-course studies on sinapine leakage (absorbance 322 nm) were made on 5 individual HK and viable seeds from the old and new lots (viability was determined later by germination testing). Single seeds were placed in 2 mL DD water and the absorbance was measured at hourly intervals using a Gilford model-250 spectrophotometer. Hourly time-course electrical conductivity measurements were determined for HK and randomly chosen old lot seeds by submerging single seeds in 1 mL DD water. Conductivity was measured for each seed using an automatic seed analyzer computer (ASAC-1000, Neogen Corp., Lansing, Mich., U.S.A.). Measurements are expressed as $\mu$amperes ($\mu$A). After an 8 h soak, seeds were transferred to moistened germination blotters for viability determinations. The conductivity measurements for leachate solutions of 5 known viable, non-viable, and heat-killed seeds were chosen at random.

Viability determination trials were conducted on 400 randomly-chosen seeds from the old and new lots. Two trials were performed on each seedlot. Single seeds were submerged in 1 mL DD water for 8 h. The water was aerated prior to commencement of the study. Four measurements were obtained from each seed: conductivity, leachate solution color, leachate solution absorbance and germination. Conductivity of the leakage solution from each seed was then determined as previously described, and seeds were transferred to moistened germination blotters. Care was taken to insure that each seed could be identified with its leachate solution. To each leachate solution 1 mL of 100 mM $K_3PO_4$ was added, a visual determination of solution color was made, and the absorbance at 390 nm was recorded for measurement of sinapine using the spectrophotometer in the visible range. It is assumed that the concentration of sinapine was proportional to the absorbance reading (Blair and Reichert, 1984, *supra*). A partition coefficient to predict seed viability was calculated for each leakage measurement technique. For electrical conductivity and absorbance readings, a partition coefficient was derived from data of individual seeds from both lots and both trials using the histogram segment method (HSM; Neogen Corp., Lansing, Mich., U.S.A.). Solution color was also used as a predictive technique, a yellow colored leachate indicated a non-viable seed, a clear solution indicated a viable seed. All germination tests were conducted according to AOSA rules. Seeds and seedlings were classified into normal, abnormal, and non-viable categories.

RESULTS AND DISCUSSION

Sinapine and electrolyte leakage for Heat-killed and viable cabbage seeds

Figure 1:
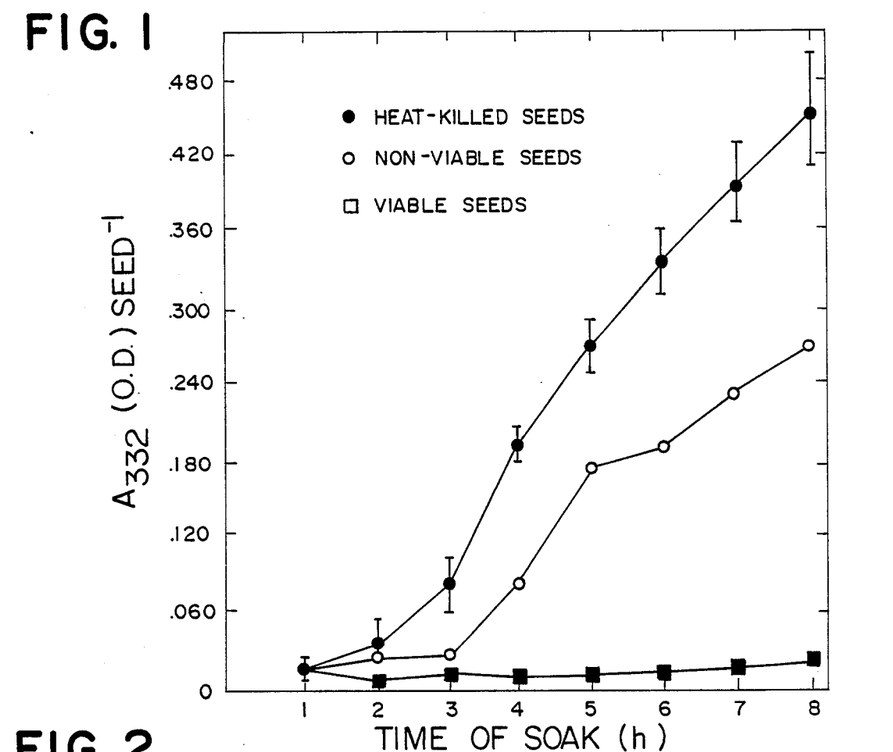
FIG. 1 is a graphic presentation of the time course of leakage for compounds absorbing at 322 nm from heat-killed (●) and viable seeds (■) and from a single non-viable (o) seed. Vertical bars indicate ±SE of the means.

A time-course study showed that HK seeds leaked higher concentrations of sinapine (solution pH 7) than viable seeds (FIG. 1). During the 8 h soak, leakage of sinapine from HK seeds exhibited a steeper linear increase pattern ($y = -0.092 + 0.069 \times O.D.$ seed$^{-1}$h$^{-1}$, $R^2 = 0.98$) than leakage from viable seeds ($y = -0.002 + 0.006 \times O.D.$ seed$^{-1}$h$^{-1}$, $R^2 = 0.90$). The leakage pattern for the one non-viable seed studied was similar to the HK seeds, although the concentration of sinapine leaked was lower.

Figure 2:
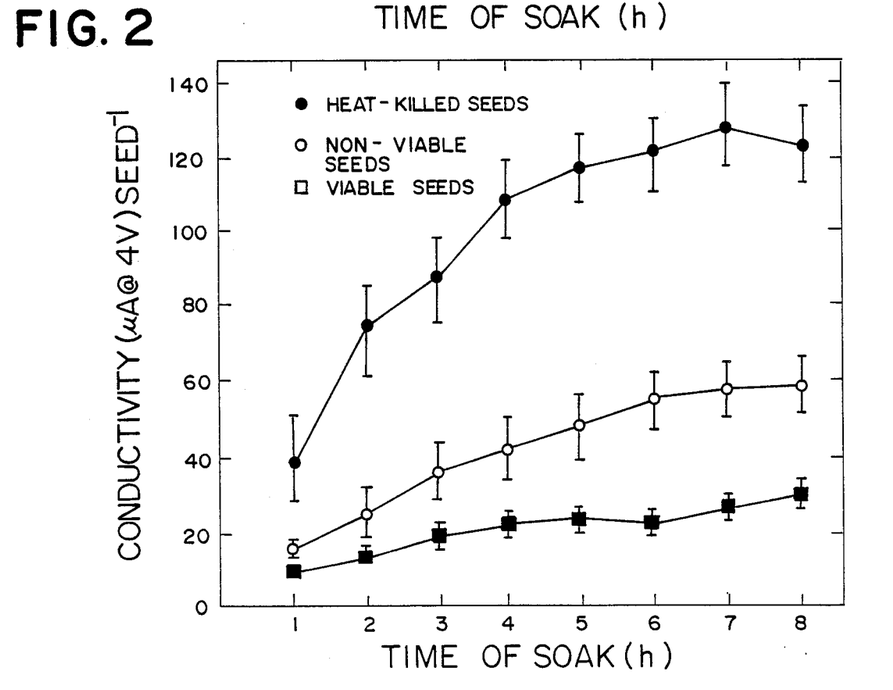
FIG. 2 is a graphic presentation of the time course of electrolyte leakage from heat-killed (●), non-viable (o), and viable seeds (■). Data points are means from 5 seeds measured individually. Vertical bars indicate ±SE of the means.

After 8 h of soaking, the mean absorbance measurements of sinapine for HK seeds (0.450 O.D.) and the non-viable seed (0.270 O.D.) were 26 and 16 times higher respectively than for the viable seeds (0.017 O.D.). Mean conductivity measurements for HK (122 $\mu$A) and non-viable (58 $\mu$A) seed treatments were only 4 times and 2 times, larger than for viable seeds (29 $\mu$A), respectively (FIG. 2). The larger differences among seed treatments for leakage of sinapine than for electrolyte leakage indicates that better differentiation between non-viable and viable seeds may be obtained using sinapine leakage rather than conductivity measurements.

Figure 3:
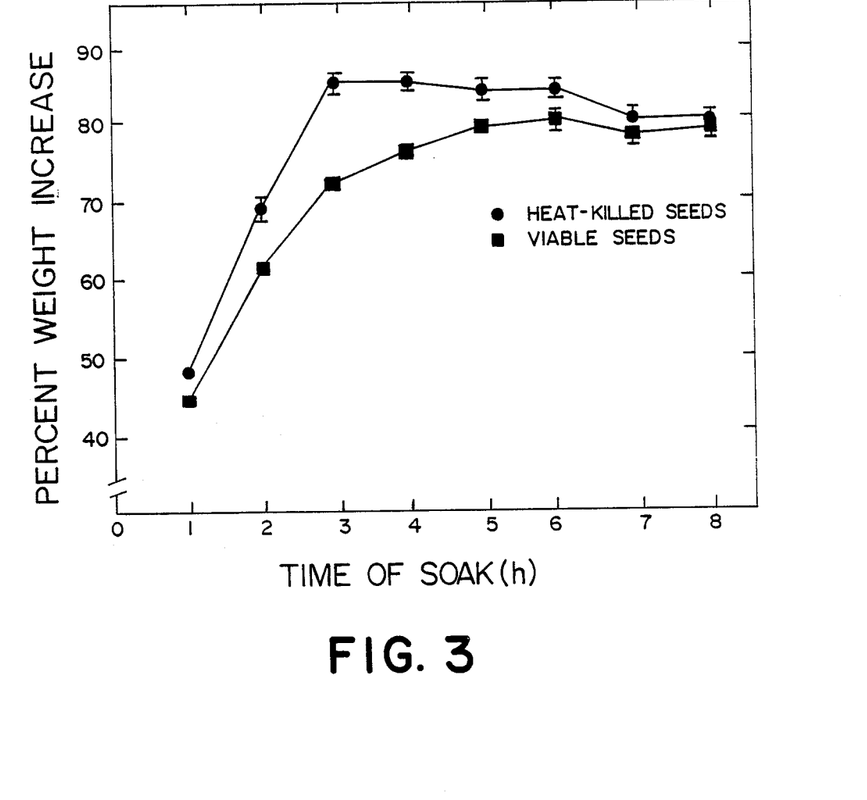
FIG. 3 is a graphic presentation of the weight increase during imbibition for heat-killed (●) and viable (■) seeds. Data points are means of 4 100-seed samples. Vertical lines indicate ±SE of the means.

Differences were observed between the imbibition pattern of HK and viable seeds (FIG. 3). Compared to viable seeds, HK seeds imbibed water faster, imbibed more water, and lost weight after 7 h of soaking (FIG. 3). HK seeds of radish have also been reported to have higher imbibition rates and imbibe more water than viable seeds, possibly by eliminating the membrane barrier to hydration (Murphy and Noland, 1982). Electrolyte leakage exhibited a significant linear relationship with imbibition rates for both HK ($R^2 = 0.98$) and viable ($R^2 = 0.98$) seed treatments during the first 3 h of soaking. However, sinapine leakage was not related to imbibition rates for either seed treatment. The rapid leakage phase for sinapine did not occur until the HK seeds were fully imbibed. This observed lag phase in sinapine leakage may be attributed to slow diffusion rates of the compound from the seed into the environment.

Detection of sinapine and electrolyte leakage as possible viability tests

A series of experiments were conducted to determine if differences detected between the sinapine leakage of viable and HK seeds could effectively differentiate viability of randomly chosen individual seeds. HK seeds were not used in the following experiments. Two seedlots that had undergone different degrees of natural aging were used. Seeds of the old lot tended to have a higher percentage non-viable and abnormal seed, as well as a reduced hypocotyl growth (after 72 h of soaking) compared to seeds of the new lot (Table 1).

TABLE 1

Standard germination and hypocotyl growth measurements for new and old cabbage seedlots.

| Seedlot | Parameter | Percentages within germination classes | | | Hypocotyl[a] growth (nm) |
|---|---|---|---|---|---|
| | | Normal | Abnormal | Non-viable | |
| Old | Mean | 92.8 | 4.0 | 3.2 | 8.6 |
| | SE | 1.5 | 0.8 | 0.8 | 0.4 |
| New | Mean | 95.8 | 2.8 | 1.4 | 10.5 |
| | SE | 1.1 | 0.8 | 0.7 | 0.6 |

[a]Hypocotyl growth measured 72 h after start of imbibition.

Seeds of both lots were subsequently classed into germination categories, and conductivity and sinapine measurements for the leachate solutions from the first soaking trials are presented in Table 2. Results of the second soaking trials were similar (data not shown). In each germination class, mean conductivity values for seeds of the new lot were higher than for seeds of the old lot. Conductivity differences between seedlots could not be explained solely by seed weight differences, although the mean seed weight for the new lot was 23% higher than for the old (4.87 mg seed$^{-1}$ and 3.74 mg seed$^{-1}$, respectively). Conductivity values for the new lots were 56% higher for normal and abnormal seedlings and 35% higher for dead seeds. A proportion ratio (conductivity for a particular germination class/normal germination class conductivity) calculated to compare differences between normal, abnormal, and non-viable seeds within and between lots (after Hepburn et al., 1984, supra) revealed that abnormal-classed seeds (1.3) were more closely associated with normal-classed seeds (1.0) than non-viable seeds (1.8 and 2.7 for the new and old lots, respectively). Similar results for abnormal seedlings have been reported for peas and soybeans (Hepburn et al., 1984, *supra*).

Better differentiation among the germination classes was achieved by measuring absorbance at 388 nm than conductivity readings. The mean sinapine measurement for non-viable seeds was 20- to 30-times higher than for normals for the old and new seedlots, respectively. Generally, a yellow color was observed for leakage solutions with sinapine absorbance measurements of 30 or greater and the color became more vivid with increased sinapine concentration. A similar yellow soak-water reaction has been reported for non-viable seeds of peppergrass (*Lepidium sativum* L.) (Lesage 1911, 1922, *Comp. Rendus*, 152:615–617 and 174:766–767). Unlike conductivity measurements, sinapine measurements across seed classes were not affected by seedlot.

TABLE 2

Conductivity and absorbance means for normal, abnormal, and non-viable germination classes of two cabbage seed lots[a].

| | | Conductivity measurements (µA) | | |
|---|---|---|---|---|
| Seedlot | Parameter | Normal | Abnormal | Non-viable |
| Old | Mean | 29.7 | 39.7 | 80.7 |
| | SE | 0.5 | 2.2 | 6.7 |
| | Proportion Ratio | 1.0 | 1.3 | 2.7 |
| New | Mean | 68.1 | 89.3 | 123.5 |
| | SE | 1.3 | 6.6 | 14.9 |
| | Proportion Ratio | 1.0 | 1.3 | 1.8 |

| | | Absorbance measurements (OD. at 388 nm) | | |
|---|---|---|---|---|
| Seedlot | Parameter | Normal | Abnormal | Non-viable |
| Old | Mean | 7.7 | 13.8 | 235.2 |
| | SE | 0.4 | 4.1 | 52.6 |
| | Proportion Ratio | 1.0 | 1.8 | 30.5 |
| New | Mean | 10.1 | 68.5 | 207.5 |
| | SE | 0.5 | 28.9 | 58.9 |
| | Proportion Ratio | 1.0 | 6.8 | 20.5 |

[a]Germination percentages for seeds after the test procedure were 83.5% normal, 9.8% abnormal, and 6.7% non-viable for the old lot, and 94.2% normal, 4.2% abnormal, and 1.6% non-viable for the new lot.

Results of the reliability of determining if an individual seed is non-viable using these 3 partition coefficients for 2 trials of each seedlot, are presented in Table 3. The solution color and absorbance partition detected a significantly higher percentage of the non-viable seeds (76 and 72%, respectively) than the conductivity partition (28%). Evidently, the detection of sinapine in soakwater better predicted non-viable seeds than the conductivity partition.

TABLE 3

Percentage of known non-viable seeds indicated to be non-viable by the different detection methods for cabbage seedlots.

| | | | Detection Method | |
|---|---|---|---|---|
| | | | Sinapine Leakage | |
| Seedlot | Trial | Conductivity | Solution Coloring | Absorbance |
| New | 1 | 50 | 100 | 100 |
| New | 2 | 36 | 73 | 64 |
| Old | 1 | 26 | 70 | 70 |
| Old | 2 | 0 | 67 | 57 |
| Mean | | 28.0B[a] | 76.0A | 72.2A |
| SE | | 10.6 | 8.0 | 9.2 |

[a]Means followed by a different letter are significantly different according to the Duncan-Waller multiple range test, $P \leq 0.05$.

The frequency and types of errors committed among the individual seeds tested in each trial indicated that the different prediction methods were prone to make different types of errors (Table 4). Error I was committed when a method predicted that a seed was non-viable yet the seed germinated. Error II was committed when a method predicted that a seed was viable when it did not germinate. Although the individual error rates for all trials were 5% or less, sinapine leakage methods tended to make more error Is and less error IIs than the conductivity partitions. The sinapine leakage methods committed fewer error IIs in trials involving the old lot than the new lot. The reason for the higher error I rate for the solution color and absorbance partition methods was that some seeds which germinated abnormally leaked solutes in high enough concentrations to be detected by these methods. The range in the percentage of abnormal seeds predicted as non-viable was from 33 to 79%. The conductivity method predicted fewer abnormals to be non-viable.

An explanation for the higher frequency of error IIs for viability prediction of old lot seeds may be due to an interaction between the length of the soaking test and the degree of aging that these seeds have undergone. The old lot seeds may have been more prone to damage caused by oxygen deprivation and soaking injury than the new lot seeds. The 8 h soak without supplemental oxygen supply (although the water was aerated before soaking began) may have caused some seeds in the old lot to die. This type of seed death may not have been accompanied by an increase in solute or electrolyte leakage.

TABLE 4

Reliability of the conductivity partition and sinapine detection absorbance partition, and solution color methods to predict seed viability.

| | | Percentage of Errors Made | | | | | |
|---|---|---|---|---|---|---|---|
| | | | | Sinapine detection | | | |
| | | Conductivity | | Solution Coloring | | Absorbance | |
| Seedlot | Trial | Error I[a] | Error II[b] | Error I | Error II | Error I | Error II |
| New | 1 | 3.8(0.2)[c] | 0.8 | 2.8(1.0) | 0.0 | 3.8(1.8) | 0.0 |
| New | 2 | 1.5(0.5) | 1.8 | 2.5(1.8) | 0.8 | 1.5(0.5) | 0.8 |
| Old | 1 | 0.2(0.0) | 5.0 | 1.0(0.8) | 2.0 | 1.0(0.8) | 2.0 |
| Old | 2 | 0.0(0.0) | 5.0 | 3.2(2.2) | 2.0 | 2.0(1.2) | 2.5 |
| Mean | | 1.4 | 3.1 | 2.4 | 1.2 | 2.1 | 1.3 |
| SE | | 0.9 | 1.1 | 0.5 | 0.5 | 0.6 | 0.6 |

[a]Error I The detection method indicated that the seed was non-viable when the germination test showed that it was viable.
[b]Error II The detection method indicated that the seed was viable when the germination test showed that it was non-viable.
[c]Number in parenthesis is the percentage of the seeds included as non-viable by the detection method and classed as abnormal in the germination test.

High amounts of electrolytes in leakage solutions coupled with the presence of proteins, sugars, and other macromolecules have been associated with severe membrane deterioration in seeds of several species (Powell and Matthews, 1977, *J. Exp. Bot., 28:225–234;* Schoettle and Leopold, 1984, *supra*; McKersie and Stinson, 1980, *supra*). Cellular disruption has been documented on cotyledonary surfaces of grain legumes during imbibition. Sinapine is leaked in high amounts from HK and non-viable, but not viable cabbage seeds because cellular membranes are non-functional (Powell and Matthews, 1981, *supra*; Leopold, 1980, *supra*), and have lost normal material retention ability. Thus, differential leakage of sinapine may be used as a marker to identify cabbage and similar seeds that are non-viable due to membrane deterioration. This study shows that the presence of sinapine in seed soak water can be detected without the use of a spectrophotometer simply by increasing the solution pH to >10. The solution becomes yellow, the intensity dependent upon compound concentration. The presence of this material in soakwater can also be detected by UV light. Both of these techniques permit rapid, inexpensive, and accurate detection of non-viable cabbage and similar seeds on a single seed basis. This solution color technique is superior to other methods of viability determination because it avoids the need of developing partition coefficients for each lot; expensive equipment is not required for detection, and only a few minutes is necessary to read results for a hundred seeds.

EXAMPLE 3

The purposes of these studies were: first, to quantify the hydration and leakage characteristics of 6 cultivars from the Brassicaceae. Second, develop a seed coating system to adsorb sinapine which leaked from individual seeds and third, compare seedling growth characteristics by sowing non-coated, coated and fluorescence sorted coated seeds in greenhous studies.

MATERIAL AND METHODS

This study consisted of five crops representing both horticultural and agronomic Brassicas and one flower species. There were a total of six seedlots (cultivars) studied:

TABLE 5

| Genus Species | Crop | Cultivar | Seed Source |
|---|---|---|---|
| B. oleracea var. capitata | Cabbage | Danish Ballhead | Harris-Moran |
| B. oleracea var. capitata | Cabbage | King Cole | Ferry-Morse |
| B. oleracea var. capitata | Cauliflower | Snowball | Harris-Moran |
| B. oleracea var. capitata | Broccoli | Citation | Harris-Moran |
| B. napus | Canola | Westar | Agro-King |
| Ersvimum hieraciifolium | Wallflower | Orange Bedder | Harris-Moran |

Controlled deterioration was performed on samples from each seedlot to age seeds for the hydration and leakage studies only. Seeds were incubated for 48 hours at 45° C. with 20 percent moisture content which is a modification of the original procedure (Matthews, 1980, In: Seed Protection (Habblewaithe ed.) Butterworths-London pp 647–661). A standard germination test was performed on 4 replicates of 50 seeds each at 20°–30° C. (Assoc. Off. Seed Anal., 1981).

Hydration studies were conducted by immersing non-deteriorated and deteriorated seeds in $H_2O$ at 25° C. There were 4 replicates of 0.5 gram samples from each seedlot. Measurements were recorded after 1,2,4 and 6 hours. Leakage studies were conducted by immersing 4 replicates of 0.2 g samples of non-deteriorated or deteriorated seeds in 10 ml $H_2O$ at 25° C. Wallflower was further diluted and a 0.2 g sample of seed was placed in 20 ml of $H_2O$. Absorbance of the steep water was observed at 322 nm and recorded after 2,4,6,8,10 and 12 hours with a Spectronic 601 spectrophotometer (Milton-Roy Co.). Danish Ballhead was commercially treated with a fungicide and dye and was therefore not suitable for the absorbance study.

Preliminary research was conducted to develop a seed coating which would adsorb leakage from hydrated seeds. The following procedure was conducted on a 30 gram sample (batch) of seeds, 20 gram of Orange Bedder. Four separate batches were coated and each batch was considered a replication. A 30 gram sample of seeds was either soaked in aerated $H_2O$ for 4 hours at 25° C. or primed in −1.5 MPa polyethylene glycol (PEG) 8000 aerated solution at 20° C. for 24 hours. Aerated soak treatments were performed in 5×25 mm glass columns with an airstone at the base of each column. After the soaking treatment, seeds were rinsed and blotted to remove excess moisture.

The hydrated seeds were then transferred to a rotating pelleting pan (Chemical and Pharmaceutical Co.). A 10% (wt/vol) solution of Pel-gel (gum arabic, Nitrogen Corp.) was used as the binder. The solution was filtered and the pH of the binder was adjusted to pH 7 with 1N KOH. Thiram was incorporated in the binder as a chemical protectant against soil-born pathogens. The solid portion or filler of the coating consisted of a mixture of cellulose (100 uM, Sigma Chemical) and fine quartz sand (<140 mesh; Pennsylvania Sand and Glass) in a 3:1 (wt/wt). The following amounts of materials were used per batch of seeds; 5–8 ml of binder and 2.0–2.5 g of filler. The binder and filler were applied alternately during the coating process (Sooter and Millier, 1978, *Am. Soc. Ag. Eng.*, 21:1034–1039).

After coating, the seeds were dried and observed under U.V. light. The coated seeds were then sorted into two categories, non-fluorescent and fluorescent and the percentage of seeds exhibiting fluorescence was recorded. Four seed treatments were studied in emergence trials. Non-coated seeds served as the control and these seeds were not hydrated. The remaining three treatments were coated (non-sorted) and coated seeds sorted into two fractions; fluorescent and non-fluorescent. Four replicates of 50 seeds from each treatment were sown in flats containing an artificial soil media (Cornell Mix) and maintained in the greenhouse. Seven to ten days after sowing, the seedlings were classified as normal, weak normal, abnormal or dead. The classification of normal and abnormal was adopted from the Rules for Testing Seeds (Assoc. Off. Seed Anal., 1981). Weak normals exhibited less growth than normal seedlings, but did not exhibit abnormal seedling development. Dead seeds were those that did not emerge during the course of the study. The emergence of total normals (normals+weak normals), from non-coated seeds was compared to the emergence from coated seeds or non-fluorescent seeds for each seedlot. Soaking seeds in water for 4 hours at 25° C. was compared with priming seeds with −1.5 MPa PEG for 24 hours at 20° C. on seedling performance.

RESULTS

The germination data of non-deteriorated and deteriorated seeds from the six seedlots are presented in Table 6. The percent normal seedlings varied among seedlots and ranged from 74 to 98 for the non-deteriorated treatments. Danish Ballhead had the highest percentage of abnormal seedlings compared to the other seedlots. The percent dead seeds ranged from 1 to 21 and the percent abnormal seedlings was not correlated with dead seeds ($r=0.25$).

TABLE 6

The germination of non-deteriorated and deteriorated seeds from different seedlots.

| | Percent | | | | | |
|---|---|---|---|---|---|---|
| | Non-deteriorated | | | Deteriorated | | |
| Cultivar | Normal | Abnormal | Dead | Normal | Abnormal | Dead |
| Danish Ballhead | 74 | 17 | 9 | 0 | 0 | 100 |
| King Cole | 95 | 2 | 3 | 3 | 27 | 70 |
| Snowball | 98 | 1 | 1 | 4 | 8 | 88 |
| Citation | 94 | 5 | 1 | 47 | 21 | 32 |
| Westar | 74 | 5 | 21 | 0 | 3 | 97 |
| Orange Bedder | 79 | 5 | 16 | 0 | 0 | 100 |

The controlled deterioration (CD) treatments severely decreased seed quality in all seedlots. Citation was the most vigorous seedlot and had 47 percent normal seedlings after CD. King Cole and Snowball were intermediate and after CD contained 70 and 87.5 percent dead seeds, respectively. No normal seedlings were recorded in the remaining 3 seedlots.

Figure 4:
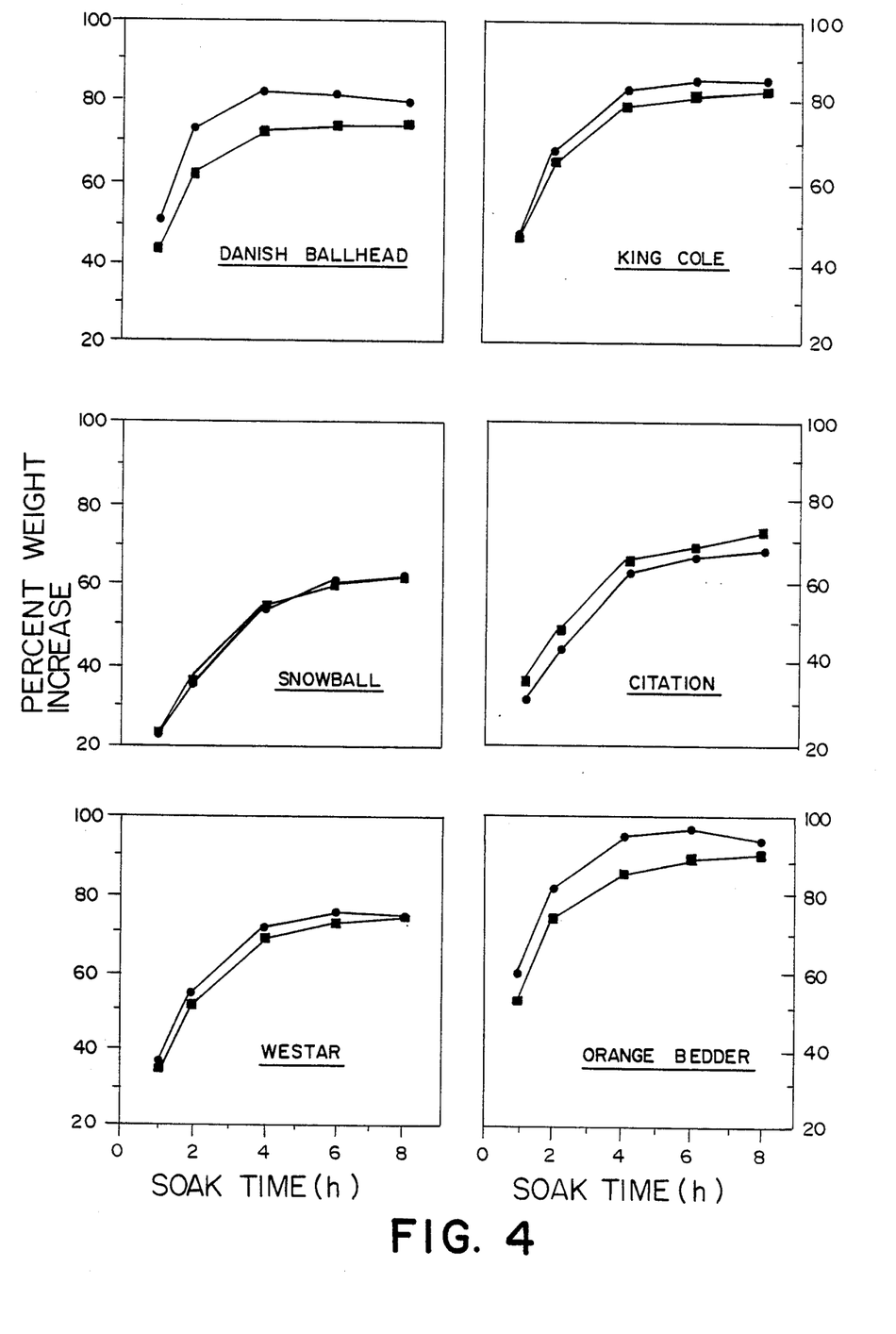
FIG. 4 shows the imbibition characteristics of (□) non-deteriorated and · deteriorated seeds from different seedlots.

The hydration study was performed to determine the length of time for full imbibition to occur. All six seedlots imbibed water in a similar manner and the percent weight ranged from 60 to 95 after a 6 hour soak (FIG. 4). The different seedlots imbibed $\geq 90$ percent of the measured weight increase after 4 hours of soaking. Only slight differences were observed between non-deteriorated and deteriorated treatments within a seedlot.

Figure 5:
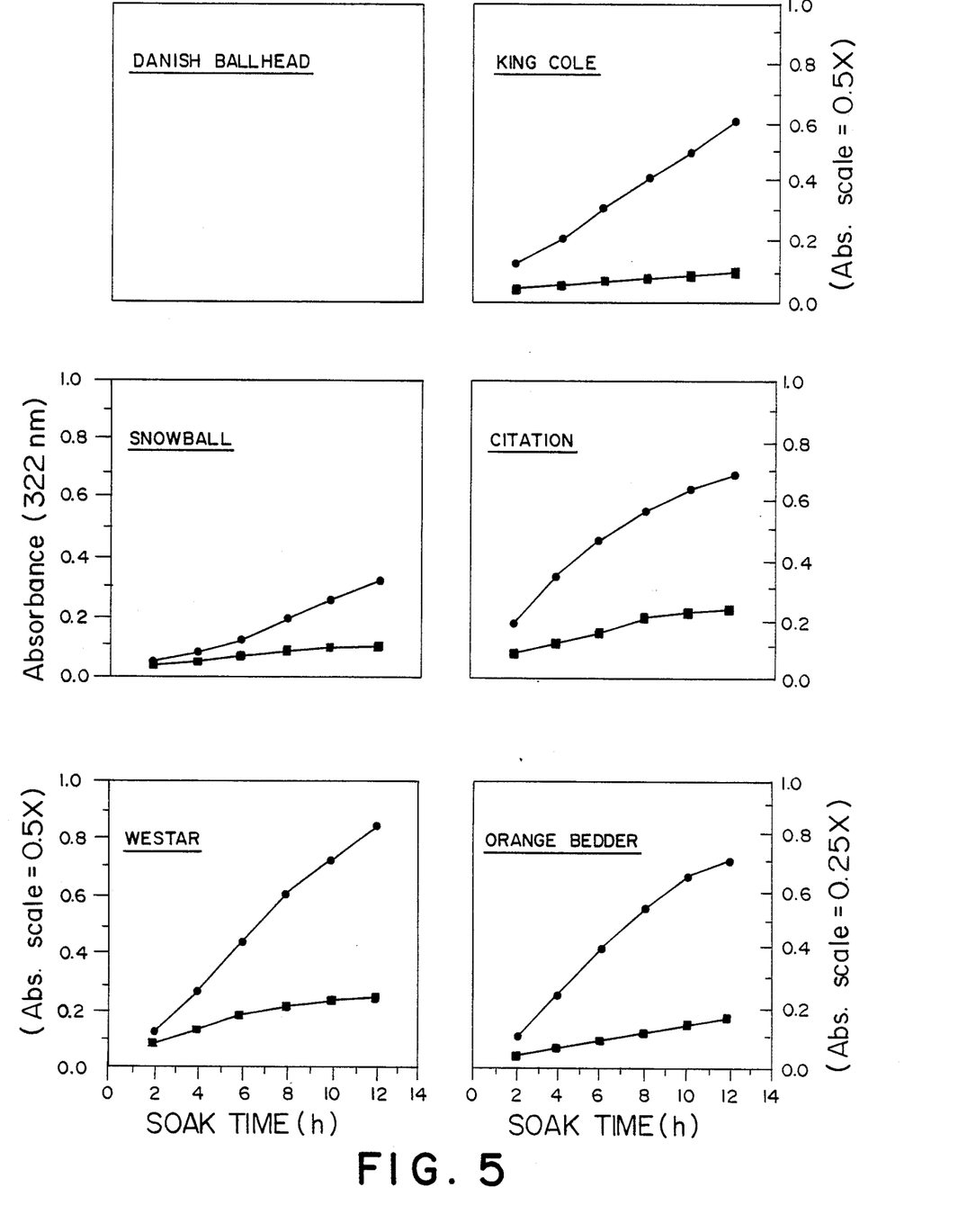
FIG. 5 shows the absorbance of leachates from (□) non-deteriorated and · deteriorated seeds from different seedlots.

The leakage studies were performed on bulk samples of both non-deteriorated and deteriorated seeds. Non-deteriorated seeds leaked less than deteriorated seeds within the same seedlot. Among the non-deteriorated treatments, King Cole, Snowball and Citation leaked less than the other seedlots (FIG. 5). Orange Bedder leaked more than the other seedlots within the non-deteriorated and deteriorated treatments. The magnitude of the differential leakage between deteriorated and non-deteriorated treatments varied among seedlots and ranged from a 1.4 to 4.0 fold increase after a 4 hour soak.

The seeds were coated, dried and then sorted under U.V. light. The percent fluorescent seeds observed was recorded (Table 7). The percent fluorescence ranged from 2.2 to 32.9 and in general was greater than the percent dead seed recorded from the non-deteriorated seeds (Table 6). The percent fluorescence was positively correlated with the percent dead seeds from the germination results ($r=0.79^*$). The primed seed had slightly less percentage fluorescence than the treatment imbibed in water.

TABLE 7

The percent fluorescent seeds after sorting from different seedlots.

| | Percent fluorescence | |
|---|---|---|
| Cultivar | Imbibed | Primed |
| Danish Ballhead | 11.0 | 9.8 |
| King Cole | 11.3 | 9.2 |
| Snowball | 2.2 | — |
| Citation | 9.8 | — |
| Westar | 21.3 | — |
| Orange Bedder | 32.9 | — |

The non-coated (control), coated, non-fluorescent and fluorescent seeds were sown in the greenhouse. The percent normal, weak normal, abnormal seedlings and dead seeds were recorded for each seedlot (Table 8). General trends were observed from the data of the 6 seedlots. The non-fluorescent treatments had a higher percentage of normal seedlings and a lower percentage abnormal seedlings and/or dead seeds compared to other treatments. The fluorescent treatment contained a higher percentage of dead seeds and poor quality seedlings than the other treatments. The fluorescent fraction produced a small percentage of normal seedlings.

TABLE 8

The percent normal, weak normal and abnormal seedlings and dead seeds from non-coated, coated, non-fluorescent and fluorescent from 6 seedlots.

| | Percent | | | |
|---|---|---|---|---|
| | Normal | Weak normal | Abnormal | Dead |
| Danish Ballhead Treatment | | | | |
| Non-coated | 52 | 21 | 15 | 12 |
| Coated non-sorted | 63 | 21 | 10 | 6 |
| Coated Non-FL | 83 | 11 | 4 | 2 |
| Coated FL | 1 | 3 | 27 | 69 |
| King Cole Treatment | | | | |
| Non-coated | 73 | 16 | 8 | 3 |
| Coated non-sorted | 80 | 14 | 4 | 2 |
| Coated Non-FL | 91 | 5 | 3 | 1 |
| Coated FL | 5 | 38 | 42 | 15 |
| Snowball Treatment | | | | |
| Non-coated | 72 | 17 | 9 | 2 |
| Coated non-sorted | 69 | 17 | 10 | 4 |
| Coated Non-FL | 86 | 9 | 3 | 2 |
| Coated FL | 1 | 10 | 39 | 50 |
| Citation Treatment | | | | |
| Non-coated | 73 | 15 | 7 | 4 |
| Coated non-sorted | 73 | 14 | 8 | 5 |
| Coated Non-FL | 90 | 6 | 4 | 0 |
| Coated FL | 1 | 15 | 51 | 33 |
| Westar Treatment | | | | |
| Non-coated | 49 | 11 | 9 | 31 |
| Coated non-sorted | 47 | 11 | 10 | 32 |
| Coated Non-FL | 72 | 11 | 7 | 10 |
| Coated FL | 4 | 8 | 4 | 84 |
| Orange Bedder Treatment | | | | |
| Non-coated | 51 | 17 | 10 | 22 |
| Coated non-sorted | 44 | 11 | 16 | 29 |
| Coated Non-FL | 70 | 17 | 10 | 3 |
| Coated FL | 5 | 14 | 16 | 64 |

Non-FL = non-fluorescent.
FL = fluorescent

The total normal seedlings obtained from non-coated seeds was compared to coated or non-fluorescent treatments. The coating procedure improved seedling emergence in both cabbage seedlots, however, coated Orange Bedder had a lower percent emergence than the non-coated seeds (Table 9).

TABLE 9

The comparison of total normal seedlings of non-coated seeds with coated and non-fluorescent seeds from 6 seedlots.

| Cultivar | Percent total normal seedlings | | | T test Non-coated vs. | |
|---|---|---|---|---|---|
| | Non-coated | Coated non-sorted | Coated Non-Fl[z] | Coated | Non-FL |
| Danish Ballhead | 73 | 84 | 94 | ** | ** |
| King Cole | 89 | 94 | 96 | ** | ** |
| Snowball | 89 | 86 | 95 | NS | ** |
| Citation | 88 | 87 | 96 | NS | ** |
| Westar | 60 | 58 | 83 | NS | ** |
| Orange Bedder | 68 | 55 | 87 | ** | ** |

[z]Non-FL = Non-fluorescent

Microbial growth was observed after germination coated Wallflower seeds on moistened blotters in preliminary research. Non-fluorescent seeds consistently outperformed non-coated seeds in each seedlot and improvements ranged from 6 to 23 percent total normal seedlings. No differences in performance were detected between soaking seeds for 4 hours and priming seeds for 24 hours (Table 10).

TABLE 10

The comparison of total normal seedlings from coated and non-fluorescent seeds with soaked and primed seeds.

| Cultivar | Seed Treatment | Percent total normal seedlings | | T test soaked vs. primed |
|---|---|---|---|---|
| | | Soaked | Primed | |
| Danish Ballhead | Coated | 74 | 76 | NS |
| | Coated Non-FL[z] | 84 | 84 | NS |
| King Cole | Coated | 91 | 90 | NS |
| | Coated Non-FL | 97 | 96 | NS |

[z]Non-FL = Non fluorescent

DISCUSSION

Five crops were studied which represented three horticultural Brassicas, one agronomic Brassica and one flower species. All seedlots had acceptable germination values and three of the seedlots produced more than 90 percent normal seedlings (Table 6). The controlled deterioration (CD) treatments greatly reduced viability and three seedlots produced no normal seedlings. Results from the standard germination tests conducted before and after CD revealed three high quality seedlots; King Cole, Snowball and Citation and three medium quality lots; Danish Ballhead, Westar and Orange Bedder.

Imbibition was monitored over time and reported as the percent weight increase (FIG. 4). The percent increase varied between seedlots which may be related to seed composition (protein content) (Leopold, 1983, *Plant Physio.*, 73:677–680). The pattern of water uptake was similar for all seedlots and appear to fit first order reaction kinetics. This trend is consistent with the kinetics of water uptake reported for other species (Leopold, 1983, *supra*).

The absorbance of the soak water at 322 nm was assumed to be directly proportional to the concentration of sinapine in solution. The time course study revealed a general linear increase in sinapine leakage and the non-deteriorated seeds leaked less than deteriorated seeds (FIG. 5). The high quality (non-deteriorated) seedlots leaked little sinapine which was attributed to the low percentage of dead seeds. Difference in leakage between seedlots may be due to seed size, seed tissue permeability or concentration of sinapine in seeds.

The sinapine leakage patterns are presented in FIG. 5. Sinapine leaks in a linear pattern from heat-killed cabbage seeds and low levels were measured from known viable seeds. The kinetics of sinapine leakage was different than electrolyte leakage as measured by the electrical conductivity of the seed steep water. Electrolytes have been reported to leak rapidly during the early phases of imbibition and then the rate decreases (Powell, 1986, *J. Seed Tech.*, 10:81–100).

A seed coating system was developed to exploit the differential leakage of sinapine associated with seed viability. Seeds were first hydrated which would cause low quality seeds to leak high levels of sinapine. Preliminary studies revealed that a 4 hour soak in aerated water was adequate to imbibe seeds and commence leakage. Seeds could also be primed in aqueous solutions of PEG and no differences in performance were observed if seeds were imbibed or primed (Table 10).

Hydrated seeds were coated in a batch process and a substance was applied which adsorbed sinapine. Finely ground cellulose was used as the adsorbent, however, aluminum oxide was also successfully tested in initial trials. Sand was added to increase the weight and density of the coating. A 10 percent solution of Pel-gel served as the binder. The pH was adjusted to pH 7 to prevent alkaline or acidic hydrolysis of the sinapine (Durkee and Thivierge, 1975, *supra*).

Emergence studies were conducted to evaluate the performance of non-coated, coated and sorted coated; non-fluorescent and fluorescent treatments. Sorting the coated seeds greatly influenced the seed quality profiles. The percent total normal seedlings was higher in the non-fluorescent than the non-coated control in all seedlots (Table 9). Though seed quality was improved after sorting by fluorescence, a small percentage of abnormal seedlings and/or dead seeds were recorded from the non-fluorescent treatments (Table 8). Seeds which produced abnormal seedlings or were dead have been shown to leak 1.8 and 30.5× more sinapine than seeds which produced normal seedlings, respectively. Thus abnormal seedlings may not have been detected due to the reduced level of leakage. All dead seeds may not have been detected for several reasons. Seed coat permeability may be different in a population of seeds which would affect the rate of sinapine diffusion. In this manner, the coating technique would not trap the sinapine and therefore the dead seeds would appear as non-fluorescent. A percentage of the seeds may have been dormant and still viable (Assoc. Off. Seed Anal. 1981). These seeds would not leak since they were viable, however they also would not germinate due to the dormancy.

The fluorescent fraction contained the highest percentage of poor quality seeds (Table 8). A small percentage of normal seedlings ($\leq 5\%$) was recorded in the fluorescent treatments. Discarding the fluorescent seeds would only eliminate from 0.02 (Snowball) to 1.6 (Orange Bedder) percent of the normal seedlings from the seedlot. Thus the technique could upgrade seed quality by reducing the percentage of abnormal seedlings and dead seeds without a significant loss of high quality seeds.

What is claimed is:

1. A method of determining the viability of crucifer seed which comprises coating the seed with a coating which is inert or beneficial to the seed, which coating absorbs sinapine and does not fluoresce at the same wave lengths as sinapine and detecting the leakage of sinapine from nonviable seed which is indicative of non-viability.

2. A method as in claim 1 where the seed has been previously soaked in an aqueous media for a time sufficient to enhance the leakage of sinapine from non-viable seed prior to said coating.

3. A method as in claim 1 where the seed coating is a cellulose based coating.

4. A method as in claim 1 where the seed coating contains a particulate absorbant for sinapine.

5. A method as in claim 1 where the leakage of the presence of sinapine is detected by measuring fluorescence indicative of sinapine.

* * * * *

UNITED STATES PATENT AND TRADEMARK OFFICE
CERTIFICATE OF CORRECTION

PATENT NO. : 4,975,364
DATED : Dec. 4, 1990
INVENTOR(S) : Alan G. Taylor et al

It is certified that error appears in the above-identified patent and that said Letters Patent is hereby corrected as shown below:

On the title page, in section [75], after "Huang,"

please change "Guangzhou, Rep. of China" to read

--Guangzhou, People's Rep. of China--.

Signed and Sealed this

Fifteenth Day of September, 1992

Attest:

DOUGLAS B. COMER

Attesting Officer    Acting Commissioner of Patents and Trademarks